United States Patent [19]
Gilmour

[11] Patent Number: 5,823,931
[45] Date of Patent: Oct. 20, 1998

[54] KNEE BRACE

[75] Inventor: Robert Farrer Gilmour, Auckland, New Zealand

[73] Assignee: Bodyworks Healthcare Limited, Auckland, New Zealand

[21] Appl. No.: 802,916

[22] Filed: Feb. 20, 1997

[51] Int. Cl.⁶ .................................................. A61F 5/00
[52] U.S. Cl. ................... 602/24; 602/16; 602/26
[58] Field of Search ................. 602/16, 23, 24, 602/25, 26

[56] References Cited

U.S. PATENT DOCUMENTS

| | | | |
|---|---|---|---|
| 3,669,105 | 6/1972 | Castiglia | 602/26 X |
| 4,503,846 | 3/1985 | Martin | 602/26 X |
| 4,607,628 | 8/1986 | Dashefsky | 602/26 |
| 4,796,610 | 1/1989 | Cromartie | 602/26 |
| 4,854,308 | 8/1989 | Drillio | 602/26 X |
| 5,018,514 | 5/1991 | Grood et al. | 602/26 X |
| 5,107,824 | 4/1992 | Rogers et al. | 602/26 X |
| 5,135,469 | 8/1992 | Castillo | 602/26 X |
| 5,302,169 | 4/1994 | Taylor | 602/26 X |

*Primary Examiner*—Linda C. Dvorak
*Attorney, Agent, or Firm*—Young & Thompson

[57] ABSTRACT

The invention provides a knee brace including stiff upper and lower arms shaped and dimensioned to fit against the medial aspects of a patient's leg above and below the knee respectively. A hinge means interconnects the arms whereby the arms are constrained for relative pivoting about a transverse axis. First and second fastening bands or straps shaped and dimensioned to encircle the leg and to be tensioned are provided, the first strap being attached to the upper arm adjacent to the hinge means for correction of varus deformity or remote from the hinge means for correction of valgus deformity, the second strap being attached to the lower arm adjacent the hinge means for correction of varus deformity or remote from the hinge means for correction of valgus deformity. Each arm includes a further location means of the respective arm to the patient's leg, each further location means being spaced remote from the first and second fastening band or straps respectively and from the knee.

16 Claims, 1 Drawing Sheet

KNEE BRACE

BACKGROUND

This invention relates to knee braces, particularly for use on humans.

Osteoarthritis of the knee is a common condition affecting middle aged and elderly people throughout the world. In recent times patients have been less accepting of the pain and activity restrictions imposed by the symptoms associated with the condition.

While knee replacement surgery or total knee arthroplasty is the definitive treatment, surgery is a last resort as current implants have a limited life span. As a result of this, conservative management options are necessary and popular. The most recent treatment option has been the use of knee braces to "unload" or stabilize the knee. Osteoarthritis involves the destruction of the articular cartilage covering the articular surfaces of the upper tibia and lower femur, within the knee joint. In most cases the medial or inside compartment of the knee wears out first. As the cartilage on the inside thins, the opposing bones move closer together resulting in the lower leg tilting inwards slightly with respect to the femur. This inward tilt is referred to as a varus deformity. If the lateral compartment is first affected then the lower leg tilts outwards. This constitutes a valgus deformity.

Once the angular deformity exists, the affected compartment is subjected to disproportionately greater loads, which in turn accelerates the destructive process. The wearing of the cartilage and resultant increased proximity of the articulating bone surfaces, is termed joint space narrowing.

The knee is stabilized on either side (medially and laterally) by the collateral ligaments. When joint space narrowing occurs these ligaments become increasingly lax and thus less effective. As a result the knee is less stable which results in the articular surfaces being less accurately opposed, during normal movement. This subjects the articular surfaces to the effects of dyskinetic movement resulting in grinding, and shear force trauma. The end result is accelerated destruction of the articular cartilage.

The object of treatment is therefore to stabilize the knee and to unload the affected compartment so as to reduce or remove pain and to halt the progress of the destructive process. The object of bracing is to unload the affected compartment, and to impart medial/lateral stability to the knee.

Most known knee braces are primarily aimed at relieving medial compartment disease. The biomechanical objective is to exert a valgus force which preloads the lateral compartment and correspondingly unloads the medial compartment. It is currently accepted that the unloading is only effective during the initial phase of gait and particularly at heel strike.

The required adjunctive action during gait is to impart medial/lateral stability to the knee in order to prevent grinding. Braces achieve this by providing a scaffold attached to the leg, above and below the knee.

Known braces use a condylar pad at the knee joint line as a critical point of force.

Various considerations relevant to the present invention may be seen from the following:

1. With medial compartment disease and any degree of varus deformity there is internal rotation of the tibia with respect to the femur during knee flexion. Therefore unless a bilateral hinge movement anticipates a rotational element, a brace with bilateral hinges will be unstable positionally with respect to the leg, and the knee joint, the biomechanical forces it exerts will be inaccurate and consequently the brace will be clinically uncomfortable for the patient, unless a single hinge is used.
2. The single hinge used is optionally adapted for the deformity of the leg at approximately 30 degrees of flexion as this is the position during which heel strike occurs. The adaption involves internal rotation of the tibial hinge arm such that at 30 degrees of flexion the brace is aligned and stable with respect to the tibia.
3. Placement of the brace should preferably be on the medial aspect of the thigh and leg as there is less mobility of the muscle profile on the medial side during gait and particularly just prior to heel strike. Thus there is enhanced positional stability during gait.
4. The lever arms exerting the valgus force should be placed as far as is practical from the joint in order to maximize efficacy.
5. The force countering the valgus moment should be centered at the joint line but applied a distance away from it if the brace is to be sufficiently comfortable during clinical application, in order to apply sufficient forces without applying a strong force at the joint line itself.

OBJECT

It is therefore an object of the present invention to go at least some distance towards meeting the foregoing desiderata in a simple yet effective manner or at least to provide the public with a useful choice.

STATEMENTS OF THE INVENTION

A knee brace including stiff upper and lower arms shaped and dimensioned to fit against the medial aspects of a patient's leg above and below the knee respectively, a hinge means interconnecting the arms whereby the arms are constrained for relative pivoting about a transverse axis, first and second fastening bands or straps shaped and dimensioned to encircle the leg and to be tensioned, the first strap being attached to the upper arm adjacent to the hinge means for correction of varus deformity or remote from the hinge means for correction of valgus deformity, the second strap being attached to the lower arm adjacent the hinge means for correction of varus deformity or remote from the hinge means for correction of valgus deformity, and each of the arm including a further location means of the respective arm to the patient's leg, each further location means being spaced remote from the first and second fastening band or straps respectively and from the knee.

Preferably the further location means includes third and fourth bands or straps attached respectively to the upper and lower arms remote from the first and second straps.

Preferably the hinge means is a bicentric hinge, which substantially parallels the biomechanics of the knee joint.

According to another aspect of the present invention there is provided a knee brace including stiff upper and lower arms shaped and dimensioned to fit against the medial faces of a patient's leg above and below the knee respectively, a hinge means interconnecting the arms whereby the arms are constrained for relative pivoting about a transverse axis, and in which the lower arm is twisted relative to the upper arm by an angle related to a varus or valgus deformity of the patient.

Preferably the angle of relative rotation between the arms is related to the angle of internal tibial rotation for varus deformity or to the angle of external tibial rotation for valgus deformity when the knee is flexed to around 30 degrees.

According to a still further aspect of the present invention there is provided a method of correction or alleviation of knee varus or valgus deformity, including the steps of measuring a patient's angle of varus or valgus deformity and angle of tibial rotation relative to the femur with the knee unflexed and when flexed at around 30 degrees, selecting a hinge means and arm configuration of the above-mentioned kind, appropriate to the angles of varus/valgus deformity and tibial rotation and incorporating the selected hinge means and arms into the knee brace.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF DRAWINGS

One embodiment of the invention is described, by way of example only, with reference to the accompanying drawings, in which.

DESCRIPTION

Figure 1:
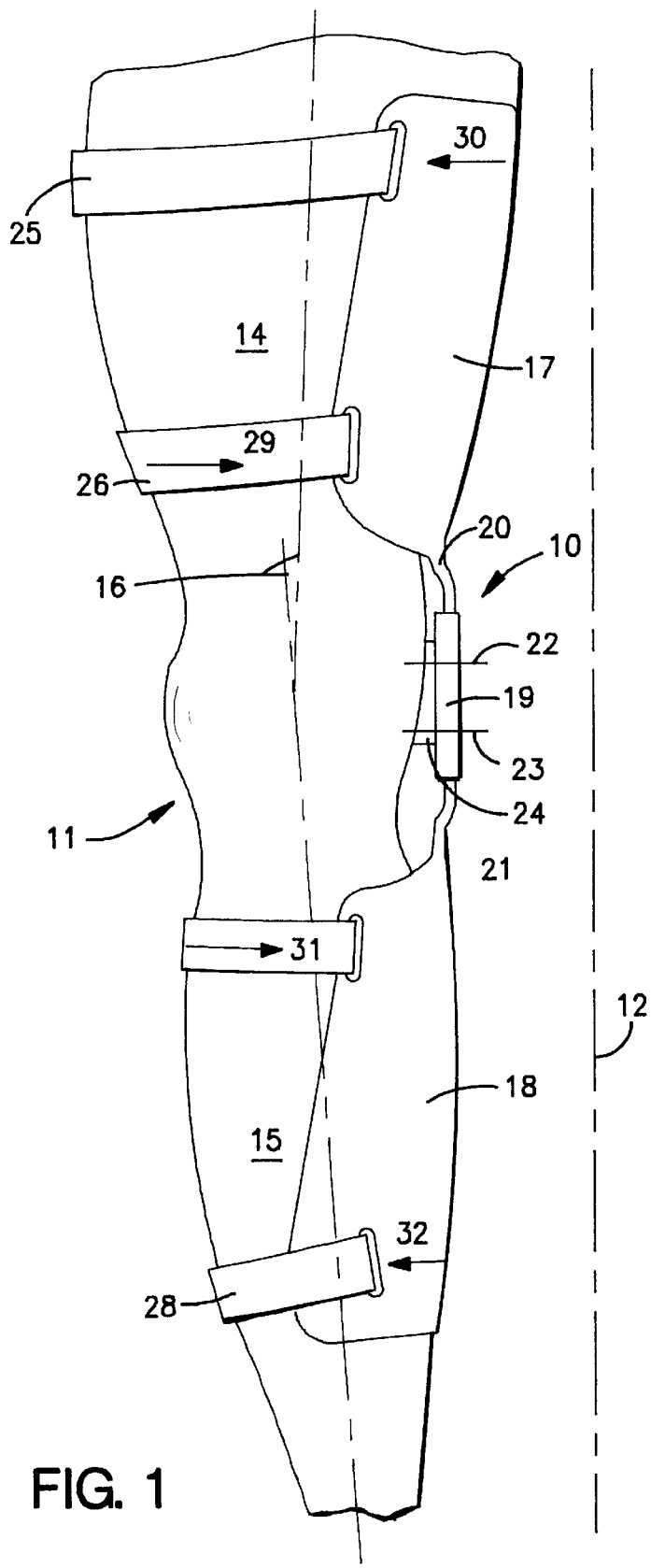
FIG. 1 is a front view of part of a patient's leg, fitted with a knee brace according to the invention.

In the drawings, a knee brace 10 is fitted to a leg 11 of a patient, whose body center line is 12. The leg 11 includes a knee 13, upper leg 14 and lower leg 15. The leg 11 shown in the drawings has an angle of varus deformity 16.

The knee brace 10 includes stiff upper and lower arms 17, 18 shaped and dimensioned to fit comfortably against the soft tissues of the medial faces of the upper and lower leg 14, 15 respectively. The arms 17, 18 are joined by hinge means 19, which is preferably a bicentric hinge of a kind known per se and which has upper and lower levers 20, 21 pivoted on axes 22, 23. A soft condylar pad 24 may be mounted on the inner surface of the hinge means 19.

The arms 17, 18 are as long as convenient for the patient, since increasing arm length reduces the magnitude of localized force applied to the leg 11 in order to achieve a required degree of correction of the deformity.

The brace 10 is fastened to the leg 11 by first, second, third and fourth bands or straps 25, 26, 27, 28 respectively. The straps 25 to 28 may be of any suitable material and width but are preferably broad and of neoprene. They may be fastened at the required tension by fastenings such as buckles, hooks and eyes, patches of hook-and-loop fastening material or the like. Padding may be provided on the straps 25 to 28, especially on those required to sustain tensile force and thereby impose localized pressure on the leg 11.

In use, reduction of the deformity angle 16 is achieved by applying a first couple to the upper leg 14 and a second couple to the lower leg 15. In FIG. 1 the first couple is in a counter-clockwise direction and the second couple is in a clockwise direction.

The angle between the levers 20, 21 in a transverse sense, or between the arms 17, 18 is chosen so as to match the angle between the upper and lower legs 14, 15 at which the required degree of varus correction would be achieved. To allow for flexure of the levers 20, 21 or the arms 17, 18 or for localized deformity of the leg musculature, the unloaded angles between the levers 20, 21 and/or arms 17, 18 may represent an apparent over-correction.

When the brace 10, thus configured, is applied to the leg 11 it will contact the leg 11 initially near the upper and lower ends of the arms 17, 18 respectively, i.e., in the region of the straps 25 and 28. The straps 26 and 27 are then passed round the leg 11, and tensioned appropriately and fastened. The tension in the strap 26 will apply a force 29 to the leg, the area of the arm 17 level with the strap 26 applying comparatively little or no pressure on the leg. The tension in the strap 26 is reacted by a force 30 applied to the leg by the upper end of the arm 17. The forces 29, 30 constitute the first couple.

Similarly, the strap 27 is tensioned and fastened, which generates forces 31, 32 on the lower leg. The forces 31, 32 constitute the second couple. Whilst the straps 25, 28 take no significant part in the above force-generating process, they serve particularly to stabilize the arms 17, 18 on the leg 11.

As mentioned above, varus deformity produces internal tibial rotation relative to the femur. Valgus deformity produces external tibial rotation. To achieve comfortable and effective fit and operation of the brace 10, the levers 20, 21 are twisted relative to each other and relative to the hinge means 19 by an amount related to the actual tibia to femur rotation angle, when the knee is flexed to the heel strike position. i.e., around 30 degrees flex angle.

Figure 2:
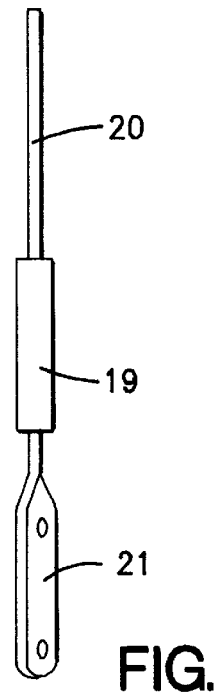
FIG. 2 is a front view of a hinge means used in FIG. 1.
Figure 3:
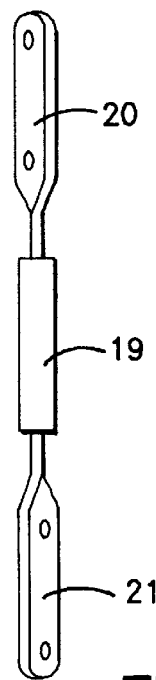
FIG. 3 is an alternative to FIG. 2.

FIGS. 2 and 3 show alternative forms of twisting of the levers 20, 21.

A further factor which has to be allowed for is the offset distance in the levers 20, 21 which can be seen in FIG. 1. The offset may be about 0.5 cm (3/16 inch) at a point about 2.5 cm above and below the hinge.

By the construction adopted in the brace 10, it is not necessary to apply any transverse force in the region of the knee 13 itself. However, if required, the condylar pad 24 can be fitted to the hinge means 19 or thereabouts. The condylar pad described in our copending New Zealand Patent Application 299954 may be used.

Where the patient suffers from a valgus deformity, the brace 10 is still fitted in the medial position on the leg 11. However, in this case the sense of rotation of the first and second couples are reversed. Consequently, tension is generated in the first and fourth straps 25, 28 rather than in the straps 26, 27. Pressure is applied to the upper and lower legs 14, 15 in the region of the bottom of the upper arm 17 and of the top of the lower arm 18.

Although the invention described above has related to the preferred medial location of the brace 10 on the leg 11 it can be used less effectively in the lateral position on the leg 11. In that case the distribution of forces for correction of a valgus deformity will be similar to that described above for a varus deformity, and vice versa.

The knee brace of the invention may be custom made to specific patients by selecting the rotation of the hinge arms and the offsets. Of course for an "off the shelf" brace standard rotations and offsets will be provided.

What I claim is:

1. A knee brace for a leg of a patient having a varus or valgus deformity, the knee brace comprising:

stiff upper and lower arms to fit against medial faces of the leg above and below a knee of the patient, respectively, said lower arm being fixedly twisted relative to said upper arm by an angle related to the varus or valgus deformity so as to limit tibial rotation; and hinge means for longitudinally pivotably interconnecting said arms and for constraining said arms from pivoting relative to each other about a transverse axis.

2. A knee brace as claimed in claim 1 wherein the angle of between the arms is related to the transverse angle of internal tibial rotation for varus deformity or to the angle of external tibial rotation for valgus deformity when the knee is flexed to around 30 degrees.

3. A knee brace as claimed in claim 1, further comprising first and second fastening straps to encircle the leg and to be tensioned, said first strap being attached to said upper arm, said second strap being attached to said lower arm.

4. A knee brace as claimed in claim 3, further comprising third and fourth straps attached respectively to said upper and lower arms remote from said first and second straps.

5. A knee brace as claimed in claim 1, wherein said hinge means is a bicentric hinge, which substantially parallels biomechanics of a knee joint.

6. A method of correcting a knee varus or valgus deformity, the method comprising the following steps:

measuring an angle of varus or valgus deformity and an angle of tibial rotation relative to a femur when a knee is unflexed and when flexed at around 30 degrees;

selecting an angular offset between stiff upper and lower arms that fit against medial faces of a leg above and below the knee, respectively, the angular offset being related to the measured angles so as to limit tibial rotation;

connecting the arms with a hinge that constrains the arms from pivoting relative to each other about a transverse axis; and affixing a knee brace having the arms and the hinge to a patient in need thereof.

7. A method of correcting a knee varus or valgus deformity, the method comprising the following steps:

measuring an angle of varus or valgus deformity and an angle of tibial rotation relative to a femur when a knee is unflexed and when flexed at around 30 degrees;

selecting a linear offset between stiff upper and lower arms that fit against medial faces of a leg above and below the knee, respectively;

connecting the arms with a hinge that constrains said arms from pivoting relative to each other about a transverse axis, the linear offset being related to the measured angles so as to limit tibial rotation; and affixing a knee brace having the arms and the hinge to a patient in need thereof.

8. A knee brace for a leg of a patient having a varus or valgus deformity, the knee brace comprising:

stiff upper and lower arms to fit against medial faces of the leg above and below a knee of the patient, respectively; and hinge means for longitudinally pivotably interconnecting said arms and for constraining said arms from pivoting relative to each other about a transverse axis, at least one of said arms being offset along a length thereof relative to said hinge means by a distance related to the varus or valgus deformity so as to limit tibial rotation.

9. A knee brace as claimed in claim 8, further comprising first and second fastening straps to encircle the leg and to be tensioned, said first strap being attached to said upper arm, said second strap being attached to said lower arm.

10. A knee brace as claimed in claim 9, further comprising third and fourth straps attached respectively to said upper and lower arms remote from said first and second straps.

11. A knee brace as claimed in claim 8, wherein said hinge means is a bicentric hinge, which substantially parallels biomechanics of a knee joint.

12. A knee brace as claimed in claim 8, wherein said lower arm is fixedly twisted relative to said upper arm by an angle related to the varus or valgus deformity so as to limit tibial rotation.

13. A knee brace as claimed in claim 12, wherein the angle between the arms is related to the angle of internal tibial rotation for varus deformity or to the angle of external tibial rotation for valgus deformity when the knee is flexed to around 30 degrees.

14. A knee brace as claimed in claim 12, further comprising first and second fastening straps to encircle the leg and to be tensioned, said first strap being attached to said upper arm, said second strap being attached to said lower arm.

15. A knee brace as claimed in claim 14, further comprising third and fourth straps attached respectively to said upper and lower arms remote from said first and second straps.

16. A knee brace as claimed in claim 12, wherein said hinge means is a bicentric hinge, which substantially parallels biomechanics of a knee joint.

\* \* \* \* \*

UNITED STATES PATENT AND TRADEMARK OFFICE
CERTIFICATE OF CORRECTION

PATENT NO. : 5,823,931
DATED : October 20, 1998
INVENTOR(S) : Robert Farrer GILMOUR It is certified that error appears in the above-indentified patent and that said Letters Patent is hereby corrected as shown below:

On the title page, insert Item [30] as follows:

--[30]   Foreign Application Priority Data

February 21, 1996    [NZ]    New Zealand........286038--.

Signed and Sealed this

Second Day of March, 1999

Attest:

Q. TODD DICKINSON

*Attesting Officer*       *Acting Commissioner of Patents and Trademarks*